United States Patent
Möckel et al.

(10) Patent No.: US 6,913,908 B2
(45) Date of Patent: Jul. 5, 2005

(54) METHODS OF MAKING L-AMINO ACIDS IN CORYNEFORM USING THE SIGE GENE

(75) Inventors: Bettina Möckel, Düsseldorf (DE); Thoams Hermann, Bielefeld (DE); Mike Farwick, Bielefeld (DE); Michael Binder, Steinhagen (DE); Walter Pfefferle, Halle (DE)

(73) Assignee: Degussa AG, Dusseldorf (DE)

( * ) Notice: Subject to any disclaimer, the term of this patent is extended or adjusted under 35 U.S.C. 154(b) by 223 days.

(21) Appl. No.: 09/935,757

(22) Filed: Aug. 24, 2001

(65) Prior Publication Data

US 2002/0103356 A1 Aug. 1, 2002

Related U.S. Application Data

(60) Provisional application No. 60/295,009, filed on Jun. 4, 2001.

(30) Foreign Application Priority Data

Sep. 2, 2000 (DE) ......................................... 100 43 336
May 31, 2001 (DE) ......................................... 101 26 422

(51) Int. Cl.$^7$ ................................................ C12P 13/04
(52) U.S. Cl. ...................................... 435/106; 435/115
(58) Field of Search ................................. 435/106, 115

(56) References Cited

U.S. PATENT DOCUMENTS

2002/0197605 A1 * 12/2002 Nakagawa et al. ............ 435/6

FOREIGN PATENT DOCUMENTS

DE          195 48 222      6/1997
EP          0864 654        9/1998
EP          1 108 790       6/2001

OTHER PUBLICATIONS

Database EMBL; Accession No. MSU87307, Mycobacterium smegnatis sigE gene (May, 1997).
Wu et al., "A mycobacterial extracytoplasmic function sigma factor involved in survival following stress", Journal of Bacteriology, vol. 179, No. 9, 1997, p. 2922–2929.
Eggeling et al., "L–glutamate and L–lysine: traditional products with impetuous developments", Appl. Microbiol. Biotechnol. vol. 52, 1999, p. 146–153.

* cited by examiner

*Primary Examiner*—Kathleen Kerr
(74) *Attorney, Agent, or Firm*—Pillsbury Winthrop Shaw Pittman LLP

(57) ABSTRACT

The present invention relates lo an isolated polynucleotide from *Corynebacterium glutamicum* comprising a polynucleotide sequence chosen from the group c insisting of (a) a polynucleotide which is identical to the extent of at least 70% to a polynucleotide which codes for a polypeptide which comprises the amino acid sequence of SEQ ID NO: 2; (b) a polynucleotide which codes for a polypeptide which comprises an amino acid sequence which is identical to the extent of at least 70% to the amino acid sequence of SEQ ID NO: 2; (c) a polynucleotide which is complementary to the polynucleotides of(a) or (b), and (d) a polynucleotide comprising at least 15 successive nucleotides of the polynucleotide sequence of (a), (b), or (c), and a process for the fermentative preparation of L-amino acids using coryneform bacteria in which at least the sigE gene is present in enhanced form, and the use of polynucleotides which comprise the sequence according to the invention as hybridization probes.

14 Claims, 2 Drawing Sheets

Figure 1: Map of the plasmid pEC-T18mob2
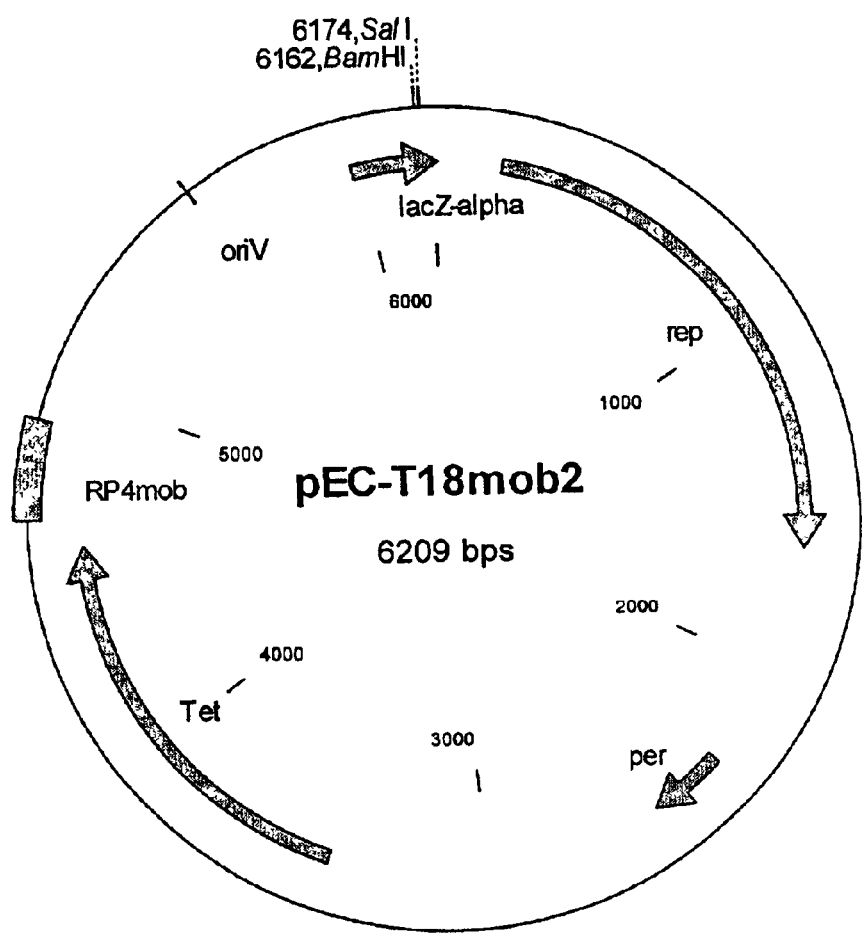

Figure 2: Map of the plasmid pEC-T18mob2sigEexp
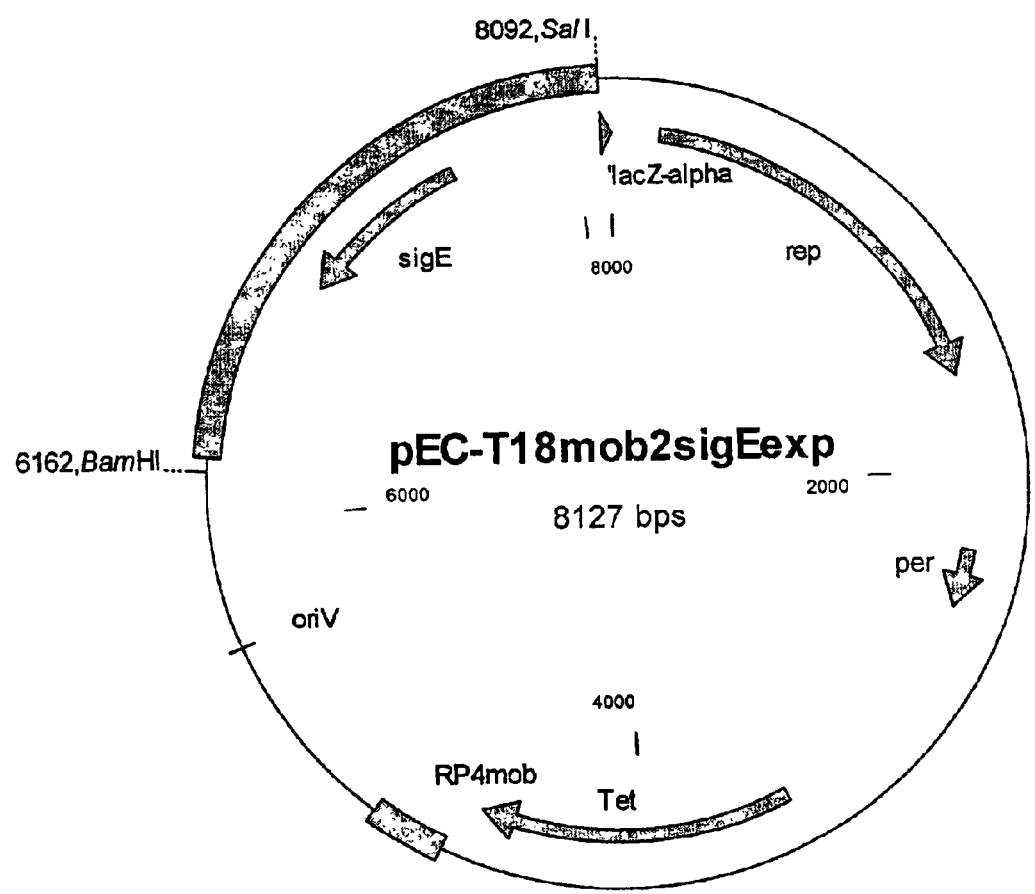

SEQUENCE LISTING

<160> NUMBER OF SEQ ID NOS: 8

<210> SEQ ID NO 1
<211> LENGTH: 1330
<212> TYPE: DNA
<213> ORGANISM: Corynebacterium glutamicum
<220> FEATURE:
<221> NAME/KEY: CDS
<222> LOCATION: (302)..(949)
<223> OTHER INFORMATION: sigE gene

<400> SEQUENCE: 1

```
accagtggag ccgttgccat tggtggtggc agccaaagtg gttagcagct ggccagtcat      60
ttcatccggg gcggggagac cgaactcggc ggcgtcttca cgagcgcgcg ctacagcagc     120
gtcggtttca gtagtggact cgacataagt gcgaagatac tcgaaggcgt tactcacgcg     180
ttatagtcta gagcgagcag gcgagatgtg aagtacctac acgcattaag tgcaaatgaa     240
ttcacaattg ccagaagatg cacaggatgt aatctagatt tcccaagttc agtgggggcaa    300 a atg act tat atg aaa aag aag tcc cga gat gac gca ccc gtc gta atc     349
  Met Thr Tyr Met Lys Lys Lys Ser Arg Asp Asp Ala Pro Val Val Ile
  1               5                  10                  15
```

```
gaa acc gtt caa gca gaa cat gct gaa gaa ctc acg ggc act gca gca       397
Glu Thr Val Gln Ala Glu His Ala Glu Glu Leu Thr Gly Thr Ala Ala
         20                  25                  30 ttc gat gct gga cag gca gac atg cca aca tgg ggc gag cta gtc gca       445
Phe Asp Ala Gly Gln Ala Asp Met Pro Thr Trp Gly Glu Leu Val Ala
 35                  40                  45 gaa cat gca gat agc gtt tac cgc ctc gcg tac cgt ctt tcc ggc aac       493
Glu His Ala Asp Ser Val Tyr Arg Leu Ala Tyr Arg Leu Ser Gly Asn
         50                  55                  60 cag cac gat gct gaa gac ctg acc caa gaa aca ttc atg cgt gtc ttc       541
Gln His Asp Ala Glu Asp Leu Thr Gln Glu Thr Phe Met Arg Val Phe
 65                  70                  75                  80 cgc tcg ttg aag agc tac cag cca ggc acc ttt gag ggc tgg ctg cac       589
Arg Ser Leu Lys Ser Tyr Gln Pro Gly Thr Phe Glu Gly Trp Leu His
                 85                  90                  95 cgc atc acc acc aac ttg ttc ctt gat atg gtt cgc cac cgc ggc aag       637
Arg Ile Thr Thr Asn Leu Phe Leu Asp Met Val Arg His Arg Gly Lys
            100                 105                 110 atc cgc atg gag gcg ctg cct gaa gat tat gag cgc gtt ccg ggc aat       685
Ile Arg Met Glu Ala Leu Pro Glu Asp Tyr Glu Arg Val Pro Gly Asn
        115                 120                 125 gac atc acc cca gag cag gca tac acc gaa gct aac ctt gac cca gct       733
Asp Ile Thr Pro Glu Gln Ala Tyr Thr Glu Ala Asn Leu Asp Pro Ala
130                 135                 140 ctg cag gca gcc ctc gat gag ttg agc cca gac ttc cgc gtg gca gtg       781
Leu Gln Ala Ala Leu Asp Glu Leu Ser Pro Asp Phe Arg Val Ala Val
145                 150                 155                 160 atc ctc tgt gat gtt gtt ggt atg agc tat gac gaa atc gca gag acc       829
Ile Leu Cys Asp Val Val Gly Met Ser Tyr Asp Glu Ile Ala Glu Thr
                165                 170                 175 ctc gga gtg aaa atg ggt acc gtg cgt tcc cgt att cac cgt gga cgc       877
Leu Gly Val Lys Met Gly Thr Val Arg Ser Arg Ile His Arg Gly Arg
            180                 185                 190 agc cag ctt cgt gca agt ttg gaa gct gca gca atg acc agc gag gaa       925
Ser Gln Leu Arg Ala Ser Leu Glu Ala Ala Ala Met Thr Ser Glu Glu
        195                 200                 205 gtt tct ttg ttg gtt cca acc cac taaagttggt gtgttttctg acacgacaaa     979
Val Ser Leu Leu Val Pro Thr His
210                 215 cgcaaatgtc gtgtcatttt tgcagctcag tgcattattt tggggttcgt ggtgcggaca   1039
gggaacttat cacaggcgac atccgttttg agtagtaggt atcttggata agaagttacc   1099
cacatccttg aaagtcgaga cacaggaggt catcggaaga tatgttcaat tccgacacca   1159
ccgcgaatct ccaagctaaa agtcgagatc gtgcaggatc taaagcaaag cgcagcaggc   1219
caagttttga ttcagtagcg cgggatgttt tggatgttcg aacaaaaaca gcacaagtta   1279
aaaacaaggc taaagagttt tcctctgttg atcacctttc agcagacgcc g           1330

<210> SEQ ID NO 2
<211> LENGTH: 216
<212> TYPE: PRT
<213> ORGANISM: Corynebacterium glutamicum

<400> SEQUENCE: 2

Met Thr Tyr Met Lys Lys Lys Ser Arg Asp Asp Ala Pro Val Val Ile
 1               5                  10                  15

Glu Thr Val Gln Ala Glu His Ala Glu Glu Leu Thr Gly Thr Ala Ala
             20                  25                  30

Phe Asp Ala Gly Gln Ala Asp Met Pro Thr Trp Gly Glu Leu Val Ala
```

```
                    35                  40                  45
Glu His Ala Asp Ser Val Tyr Arg Leu Ala Tyr Arg Leu Ser Gly Asn
 50                  55                  60

Gln His Asp Ala Glu Asp Leu Thr Gln Glu Thr Phe Met Arg Val Phe
 65                  70                  75                  80

Arg Ser Leu Lys Ser Tyr Gln Pro Gly Thr Phe Glu Gly Trp Leu His
                 85                  90                  95

Arg Ile Thr Thr Asn Leu Phe Leu Asp Met Val Arg His Arg Gly Lys
                100                 105                 110

Ile Arg Met Glu Ala Leu Pro Glu Asp Tyr Glu Arg Val Pro Gly Asn
            115                 120                 125

Asp Ile Thr Pro Glu Gln Ala Tyr Thr Glu Ala Asn Leu Asp Pro Ala
130                 135                 140

Leu Gln Ala Ala Leu Asp Glu Leu Ser Pro Asp Phe Arg Val Ala Val
145                 150                 155                 160

Ile Leu Cys Asp Val Val Gly Met Ser Tyr Asp Glu Ile Ala Glu Thr
                165                 170                 175

Leu Gly Val Lys Met Gly Thr Val Arg Ser Arg Ile His Arg Gly Arg
            180                 185                 190

Ser Gln Leu Arg Ala Ser Leu Glu Ala Ala Ala Met Thr Ser Glu Glu
        195                 200                 205

Val Ser Leu Leu Val Pro Thr His
    210                 215

<210> SEQ ID NO 3
<211> LENGTH: 457
<212> TYPE: DNA
<213> ORGANISM: Corynebacterium glutamicum
<220> FEATURE:
<223> OTHER INFORMATION: upstream region

<400> SEQUENCE: 3
tagtcaccac ggttaagcct gcaccaaggg gcaggcgagc aacgtgtgcg ccttcaatgg      60
aacgaatata ttcatcggcg tcacgtgctg cttgggtgtc acgatccttg cgggtttgat     120
ccgcaatggt gccgtcaagg agcgcatcgg cgagcaccag cgcaccgcct cgtcgaagaa     180
gcggccaggc ggcgtcgaca agcgccttta aatccatggg ggagacttgg ccgaagacaa     240
gctgatagct gtcgttggca aggcgactca tcacgtcgag cgggcgcgag agcaagaagc     300
gtacgcggct gggggaatag ccggcctcgc ggaagagtgc tttggcctgg cgctgatgct     360
ctgattcagg atcaatgcag gtcagtgtgg tgttatcggc cagtccgttc aggatataca     420
gaccccaccaa cccggcagcc ggggtaatcg cgatggc                              457

<210> SEQ ID NO 4
<211> LENGTH: 299
<212> TYPE: DNA
<213> ORGANISM: Corynebacterium glutamicum
<220> FEATURE:
<223> OTHER INFORMATION: downstream region

<400> SEQUENCE: 4
cagccatgtt tgtagacaat gaactgtccc gtggcgccat gcatcgcgcc aggctgcaca      60
ttgtgcactg cgctgaatgt agggaagaga ttaaccgtca gcgggaaacc gttgattatc     120
tccgctcaga gtgcaaaaac gaagaagtgt ccgccccaat ggacctcaaa gcacggcttg     180
ccagcctcgc cactgagtgc atgcctggcc ctggcgcaga gaatttagca atgcagcgcc     240
```

-continued

```
cagagtcttt tgtggctaaa gttgagtccg tagtgcgcgc agttcgtaag aaccaaggc      299
```

<210> SEQ ID NO 5
<211> LENGTH: 2086
<212> TYPE: DNA
<213> ORGANISM: Corynebacterium glutamicum
<220> FEATURE:
<221> NAME/KEY: CDS
<222> LOCATION: (759)..(1406)
<223> OTHER INFORMATION: sigE

<400> SEQUENCE: 5

```
tagtcaccac ggttaagcct gcaccaaggg gcaggcgagc aacgtgtgcg ccttcaatgg      60
aacgaatata ttcatcggcg tcacgtgctg cttgggtgtc acgatccttg cgggtttgat     120
ccgcaatggt gccgtcaagg agcgcatcgg cgagcaccag cgcaccgcct cgtcgaagaa     180
gcggccaggc ggcgtcgaca agcgccttta aatccatggg ggagacttgg ccgaagacaa     240
gctgatagct gtcgttggca aggcgactca tcacgtcgag cgggcgcgag agcaagaagc     300
gtacgcggct gggggaatag ccggcctcgc ggaagagtgc tttggcctgg cgctgatgct     360
ctgattcagg atcaatgcag gtcagtgtgg tgttatcggc cagtccgttc aggatataca     420
gacccaccaa cccggcagcc ggggtaatcg cgatggcacc agtggagccg ttgccattgg     480
tggtggcagc caaagtggtt agcagctggc cagtcatttc atccggggcg gggagaccga     540
actcggcggc gtcttcacga gcgcgcgcta cagcagcgtc ggtttcagta gtggactcga     600
cataagtgcg aagatactcg aaggcgttac tcacgcgtta tagtctagag cgagcaggcg     660
agatgtgaag tacctacacg cattaagtgc aaatgaattc acaattgcca gaagatgcac     720
aggatgtaat ctagatttcc caagttcagt ggggcaaa atg act tat atg aaa aag     776
                                          Met Thr Tyr Met Lys Lys
                                           1               5 aag tcc cga gat gac gca ccc gtc gta atc gaa acc gtt caa gca gaa         824
Lys Ser Arg Asp Asp Ala Pro Val Val Ile Glu Thr Val Gln Ala Glu
         10                  15                  20 cat gct gaa gaa ctc acg ggc act gca gca ttc gat gct gga cag gca         872
His Ala Glu Glu Leu Thr Gly Thr Ala Ala Phe Asp Ala Gly Gln Ala
 25                  30                  35 gac atg cca aca tgg ggc gag cta gtc gca gaa cat gca gat agc gtt         920
Asp Met Pro Thr Trp Gly Glu Leu Val Ala Glu His Ala Asp Ser Val
         40                  45                  50 tac cgc ctc gcg tac cgt ctt tcc ggc aac cag cac gat gct gaa gac         968
Tyr Arg Leu Ala Tyr Arg Leu Ser Gly Asn Gln His Asp Ala Glu Asp
 55                  60                  65                  70 ctg acc caa gaa aca ttc atg cgt gtc ttc cgc tcg ttg aag agc tac        1016
Leu Thr Gln Glu Thr Phe Met Arg Val Phe Arg Ser Leu Lys Ser Tyr
                 75                  80                  85 cag cca ggc acc ttt gag ggc tgg ctg cac cgc atc acc acc aac ttg        1064
Gln Pro Gly Thr Phe Glu Gly Trp Leu His Arg Ile Thr Thr Asn Leu
         90                  95                 100 ttc ctt gat atg gtt cgc cac cgc ggc aag atc cgc atg gag gcg ctg        1112
Phe Leu Asp Met Val Arg His Arg Gly Lys Ile Arg Met Glu Ala Leu
         105                 110                 115 cct gaa gat tat gag cgc gtt ccg ggc aat gac atc acc cca gag cag        1160
Pro Glu Asp Tyr Glu Arg Val Pro Gly Asn Asp Ile Thr Pro Glu Gln
 120                 125                 130 gca tac acc gaa gct aac ctt gac cca gct ctg cag gca gcc ctc gat        1208
Ala Tyr Thr Glu Ala Asn Leu Asp Pro Ala Leu Gln Ala Ala Leu Asp
135                 140                 145                 150 gag ttg agc cca gac ttc cgc gtg gca gtg atc ctc tgt gat gtt gtt        1256
Glu Leu Ser Pro Asp Phe Arg Val Ala Val Ile Leu Cys Asp Val Val
```

-continued

```
                  155                 160                 165
ggt atg agc tat gac gaa atc gca gag acc ctc gga gtg aaa atg ggt     1304
Gly Met Ser Tyr Asp Glu Ile Ala Glu Thr Leu Gly Val Lys Met Gly
            170                 175                 180 acc gtg cgt tcc cgt att cac cgt gga cgc agc cag ctt cgt gca agt     1352
Thr Val Arg Ser Arg Ile His Arg Gly Arg Ser Gln Leu Arg Ala Ser
        185                 190                 195 ttg gaa gct gca gca atg acc agc gag gaa gtt tct ttg ttg gtt cca     1400
Leu Glu Ala Ala Ala Met Thr Ser Glu Glu Val Ser Leu Leu Val Pro
    200                 205                 210 acc cac taaagttggt gtgttttctg acacgacaaa cgcaaatgtc gtgtcatttt       1456
Thr His
215 tgcagctcag tgcattattt tggggttcgt ggtgcggaca gggaacttat cacaggcgac    1516 atccgttttg agtagtaggt atcttggata agaagttacc cacatccttg aaagtcgaga    1576 cacaggaggt catcggaaga tatgttcaat tccgacacca ccgcgaatct ccaagctaaa    1636 agtcgagatc gtgcaggatc taaagcaaag cgcagcaggc caagttttga ttcagtagcg    1696 cgggatgttt tggatgttcg aacaaaaaca gcacaagtta aaacaaggc taaagagttt     1756 tcctctgttg atcacctttc agcagacgcc gcagccatgt ttgtagacaa tgaactgtcc    1816 cgtggcgcca tgcatcgcgc caggctgcac attgtgcact cgctgaatg tagggaagag     1876 attaaccgtc agcgggaaac cgttgattat ctccgctcag agtgcaaaaa cgaagaagtg    1936 tccgccccaa tggacctcaa agcacggctt gccagcctcg ccactgagtg catgcctggc    1996 cctggcgcag agaatttagc aatgcagcgc ccagagtctt ttgtggctaa agttgagtcc    2056 gtagtgcgcg cagttcgtaa gaaccaaggc                                    2086
```

<210> SEQ ID NO 6
<211> LENGTH: 216
<212> TYPE: PRT
<213> ORGANISM: Corynebacterium glutamicum

<400> SEQUENCE: 6

```
Met Thr Tyr Met Lys Lys Lys Ser Arg Asp Asp Ala Pro Val Val Ile
 1               5                  10                  15

Glu Thr Val Gln Ala Glu His Ala Glu Glu Leu Thr Gly Thr Ala Ala
            20                  25                  30

Phe Asp Ala Gly Gln Ala Asp Met Pro Thr Trp Gly Glu Leu Val Ala
        35                  40                  45

Glu His Ala Asp Ser Val Tyr Arg Leu Ala Tyr Arg Leu Ser Gly Asn
    50                  55                  60

Gln His Asp Ala Glu Asp Leu Thr Gln Glu Thr Phe Met Arg Val Phe
65                  70                  75                  80

Arg Ser Leu Lys Ser Tyr Gln Pro Gly Thr Phe Glu Gly Trp Leu His
                85                  90                  95

Arg Ile Thr Thr Asn Leu Phe Leu Asp Met Val Arg His Arg Gly Lys
            100                 105                 110

Ile Arg Met Glu Ala Leu Pro Glu Asp Tyr Glu Arg Val Pro Gly Asn
        115                 120                 125

Asp Ile Thr Pro Glu Gln Ala Tyr Thr Glu Ala Asn Leu Asp Pro Ala
    130                 135                 140

Leu Gln Ala Ala Leu Asp Glu Leu Ser Pro Asp Phe Arg Val Ala Val
145                 150                 155                 160

Ile Leu Cys Asp Val Val Gly Met Ser Tyr Asp Glu Ile Ala Glu Thr
```

```
                        165                 170                 175
Leu Gly Val Lys Met Gly Thr Val Arg Ser Arg Ile His Arg Gly Arg
                180                 185                 190

Ser Gln Leu Arg Ala Ser Leu Glu Ala Ala Ala Met Thr Ser Glu Glu
            195                 200                 205

Val Ser Leu Leu Val Pro Thr His
        210                 215

<210> SEQ ID NO 7
<211> LENGTH: 20
<212> TYPE: DNA
<213> ORGANISM: Corynebacterium glutamicum
<220> FEATURE:
<223> OTHER INFORMATION: Primer sigE1

<400> SEQUENCE: 7
tagtcaccac ggttaagcct                                                   20

<210> SEQ ID NO 8
<211> LENGTH: 20
<212> TYPE: DNA
<213> ORGANISM: Corynebacterium glutamicum
<220> FEATURE:
<223> OTHER INFORMATION: Primer sigE2

<400> SEQUENCE: 8
gccttggttc ttacgaactg                                                   20
```

US 6,913,908 B2

METHODS OF MAKING L-AMINO ACIDS IN CORYNEFORM USING THE SIGE GENE

This claims priority to U.S. Provisional Patent Appl. No. 60/295,009, filed Jun. 4, 2001, which claims priority to German Patent Application Nos. 10126422.4 and 10043336.7. filed May 31, 2001 and Sep. 2, 2000, respectively.

FIELD OF THE INVENTION

The invention provides nucleotide sequences from coryneform bacteria which code for the sigE gene and a process for the fermentative preparation of amino acids using bacteria in which the sigE gene is enhanced.

PRIOR ART

L-Amino acids are used in human medicine and in the pharmaceuticals industry, in the foodstuffs industry and especially in animal nutrition.

It is known that amino acids are prepared by fermentation from strains of coryneform bacteria, in particular *Corynebacterium glutamicum*. Because of their great importance, work is constantly being undertaken to improve the preparation processes. Improvements to the process can relate to fermentation measures, such as, for example, stirring and supply of oxygen, or the composition of the nutrient media, such as, for example, the sugar concentration during the fermentation, or the working up to the product form by, for example, ion exchange chromatography, or the intrinsic output properties of the microorganism itself.

Methods of mutagenesis, selection and mutant selection are used to improve the output properties of these microorganisms. Strains which are resistant to antimetabolites or are auxotrophic for metabolites of regulatory importance and produce amino acids are obtained in this manner.

Methods of the recombinant DNA technique have also been employed for some years for improving the strain of *Corynebacterium* strains which produce L-amino acid, by amplifying individual amino acid biosynthesis genes and investigating the effect on the amino acid production.

OBJECT OF THE INVENTION

The inventors had the object of providing new measures for improved fermentative preparation of amino acids.

SUMMARY OF THE INVENTION

Where L-amino acids or amino acids are mentioned in the following, this means one or more amino acids, including their salts, chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine. Lysine is particularly preferred.

The invention provides an isolated polynucleotide from coryneform bacteria, comprising a polynucleotide sequence which codes for the sigE gene, chosen from the group consisting of a) polynucleotide which is identical to the extent of at least 70% to a polynucleotide which codes for a polypeptide which comprises the amino acid sequence of SEQ ID No. 2, b) polynucleotide which codes for a polypeptide which comprises an amino acid sequence which is identical to the extent of at least 70% to the amino acid sequence of SEQ ID No. 2, c) polynucleotide which is complementary to the polynucleotides of a) or b), and d) polynucleotide comprising at least 15 successive nucleotides of the polynucleotide sequence of a), b) or c), the polypeptide preferably having the activity of sigma factor E.

The invention also provides the above-mentioned polynucleotide, this preferably being a DNA which is capable of replication, comprising:

BRIEF DESCRIPTION OF THE FIGURES

FIG. 1: Map of the plasmid pET-T18mob2

FIG. 2: Map of the plasmid pET-T18mob2sigEexp

The abbreviation and designation used have the following meaning.

| | |
|---|---|
| per: | Gene for controlling the number of copies from PGA1 |
| oriV: | ColE1-similiar origin from pMB1 |
| rep: | Plasmid-coded replication region from C. glutamicum plasmid pGA1 |
| RP4mob: | RP4 mobilization site |
| lacZ-alpha: | lacZ gene fragment from E. coli |
| Tet: | Resistance gene from tetracycline |
| sigE: | sigE gene of C. glutamicum |
| BamHI: | Cleavage site of the restriction enzyme BamHI |
| SalI: | Cleavage site of the restriction enzyme SalI |
| sigE: | sigE gene of C. glutamicum |
| BamHI: | Cleavage site of the restriction enzyme BamHI |
| SalI: | Cleavage site of the restriction enzyme SalI |

(i) the nucleotide sequences shown in SEQ ID No. 1, SEQ ID NO. 3 or 4, or (ii) at least one sequence which corresponds to sequence (i) within the range of the degeneration of the genetic code, or (iii) at least one sequence which hybridizes with the sequence complementary to sequence (i) or (ii), and optionally (iv) sense mutations of neutral function in (i).

The invention also provides a polynucleotide, in particular DNA, which is capable of replication and comprises the nucleotide sequence as shown in SEQ ID No. 1;

a polynucleotide which codes for a polypeptide which comprises the amino acid sequence as shown in SEQ ID No. 2;

a vector containing the polynucleotide according to the invention, in particular a shuttle vector or plasmid vector, and coryneform bacteria which contain the vector or in which the sigE gene is enhanced.

The invention also provides polynucleotides which substantially comprise a polynucleotide sequence, which are obtainable by screening by means of hybridization of a corresponding gene library of a coryneform bacterium, which comprises the complete gene or parts thereof, with a probe which comprises the sequence of the polynucleotide according to the invention according to SEQ ID No.1 or a fragment thereof, and isolation of the polynucleotide sequence mentioned.

DETAILED DESCRIPTION OF THE INVENTION

Polynucleotides which comprise the sequences according to the invention are suitable as hybridization probes for RNA, cDNA and DNA, in order to isolate, in the full length, nucleic acids or polynucleotides or genes which code for sigma factor E or to isolate those nucleic acids or polynucleotides or genes which have a high similarity of sequence with that of the sigE gene.

Polynucleotides which comprise the sequences according to the invention are furthermore suitable as primers with the aid of which DNA of genes which code for sigma factor E can be prepared by the polymerase chain reaction (PCR).

Such oligonucleotides which serve as probes or primers comprise at least 30, preferably at least 20, very particularly preferably at least 15 successive nucleotides. Oligonucleotides which have a length of at least 40 or 50 nucleotides are also suitable.

"Isolated" means separated out of its natural environment.

"Polynucleotide" in general relates to polyribonucleotides and polydeoxyribonucleotides, it being possible for these to be non-modified RNA or DNA or modified RNA or DNA.

The polynucleotides according to the invention include a polynucleotide according to SEQ ID No. 1 or a fragment prepared therefrom and also those which are at least 70%, preferably at least 80% and in particular at least 90% to 95% identical to the polynucleotide according to SEQ ID No. 1 or a fragment prepared therefrom.

"Polypeptides" are understood as meaning peptides or proteins which comprise two or more amino acids bonded via peptide bonds.

The polypeptides according to the invention include a polypeptide according to SEQ ID No. 2, in particular those with the biological activity of sigma factor E, and also those which are at least 70%, preferably at least 80% and in particular at least 90% to 95% identical to the polypeptide according to SEQ ID No. 2 and have the activity mentioned.

The invention furthermore relates to a process for the fermentative preparation of amino acids chosen from the group consisting of L-asparagine, L-threonine, L-serine, L-glutamate, L-glycine, L-alanine, L-cysteine, L-valine, L-methionine, L-isoleucine, L-leucine, L-tyrosine, L-phenylalanine, L-histidine, L-lysine, L-tryptophan and L-arginine using coryneform bacteria which in particular already produce amino acids and in which the nucleotide sequences which code for the sigE gene are enhanced, in particular over-expressed.

The term "enhancement" in this connection describes the increase in the intracellular activity of one or more enzymes in a microorganism which are coded by the corresponding DNA, for example by increasing the number of copies of the gene or allele or of the genes or alleles, using a potent promoter or using a gene or allele which codes for a corresponding enzyme having a high activity, and optionally combining these measures.

The microorganisms which the present invention provides can produce L-amino acids from glucose, sucrose, lactose, fructose, maltose, molasses, starch, cellulose or from glycerol and ethanol. They can be representatives of coryneform bacteria, in particular of the genus *Corynebacterium*. Of the genus *Corynebacterium*, there may be mentioned in particular the species *Corynebacterium glutamicum*, which is known among experts for its ability to produce L-amino acids.

Suitable strains of the genus *Corynebacterium*, in particular of the species *Corynebacterium glutamicum* (*C. glutamicum*), are in particular the known wild-type strains

*Corynebacterium glutamicum* ATCC13032
*Corynebacterium acetoglutamicum* ATCC15806
*Corynebacterium acetoacidophilum* ATCC13870
*Corynebacterium thermoaminogenes* FERM BP-1539
*Corynebacterium melassecola* ATCC17965,
*Brevibacterium flavum* ATCC14067
*Brevibacterium lactofermentum* ATCC13869 and
*Brevibacterium divaricatum* ATCC14020 and L-amino acid-producing mutants or strains prepared therefrom.

The new sigE gene from *C. glutamicum* which codes for the sigma-E factor has been isolated.

To isolate the sigE gene or also other genes of *C. glutamicum*, a gene library of this microorganism is first set up in *Escherichia coli* (*E. coli*). The setting up of gene libraries is described in generally known textbooks and handbooks. The textbook by Winnacker: Gene und Klone, Eine Einführung in die Gentechnologie (Verlag Chemie, Weinheim, Germany, 1990), or the handbook by Sambrook et al.: Molecular Cloning, A Laboratory Manual (Cold Spring Harbor Laboratory Press, 1989) may be mentioned as an example. A well-known gene library is that of the *E. coli* K-12 strain W3110 set up in λ vectors by Kohara et al. (Cell 50, 495–508 (1987)). Bathe et al. (Molecular and General Genetics, 252:255–265, 1996) describe a gene library of *C. glutamicum* ATCC13032, which was set up with the aid of the cosmid vector SuperCos I (Wahl et al., 1987, Proceedings of the National Academy of Sciences USA, 84:2160–2164) in the *E. coli* K-12 strain NM554 (Raleigh et al., 1988, Nucleic Acids Research 16:1563–1575).

Börmann et al. (Molecular Microbiology 6(3), 317–326) (1992)) in turn describe a gene library of *C. glutamicum* ATCC13032 using the cosmid pHC79 (Hohn and Collins, Gene 11, 291–298 (1980)).

To prepare a gene library of *C. glutamicum* in *E. coli* it is also possible to use plasmids such as pBR322 (Bolivar, Life Sciences, 25, 807–818 (1979)) or pUC9 (Vieira et al., 1982, Gene, 19:259–268). Suitable hosts are, in particular, those *E. coli* strains which are restriction- and recombination-defective. An example of these is the strain DH5αmcr, which has been described by Grant et al. (Proceedings of the National Academy of Sciences USA, 87 (1990) 4645–4649). The long DNA fragments cloned with the aid of cosmids can in turn be subcloned in the usual vectors suitable for sequencing and then sequenced, as is described e.g. by Sanger et al. (Proceedings of the National Academy of Sciences of the United States of America, 74:5463–5467, 1977).

The resulting DNA sequences can then be investigated with known algorithms or sequence analysis programs, such as e.g. that of Staden (Nucleic Acids Research 14, 217–232 (1986)), that of Marck (Nucleic Acids Research 16, 1829–1836 (1988)) or the GCG program of Butler (Methods of Biochemical Analysis 39, 74–97 (1998)).

The new DNA sequence of *C. glutamicum* which codes for the sigE gene and which, as SEQ ID No. 1, is a constituent of the present invention has been found. The amino acid sequence of the corresponding protein has furthermore been derived from the present DNA sequence by the methods described above. The resulting amino acid sequence of the sigE gene product is shown in SEQ ID No. 2.

Coding DNA sequences which result from SEQ ID No. 1 by the degeneracy of the genetic code are also a constituent of the invention. In the same way, DNA sequences which hybridize with SEQ ID No. 1 or parts of SEQ ID No. 1 are a constituent of the invention. Conservative amino acid exchanges, such as e.g. exchange of glycine for alanine or of aspartic acid for glutamic acid in proteins, are furthermore known among experts as "sense mutations" which do not lead to a fundamental change in the activity of the protein, i.e. are of neutral function. It is furthermore known that changes on the N and/or C terminus of a protein cannot substantially impair or can even stabilize the function thereof. Information in this context can be found by the expert, inter alia, in Ben-Bassat et al. (Journal of Bacteriology 169:751–757 (1987)), in O'Regan et al. (Gene 77:237–251 (1989)), in Sahin-Toth et al. (Protein Sciences 3:240–247 (1994)), in Hochuli et al. (Bio/Technology 6:1321–1325 (1988)) and in known textbooks of genetics and molecular biology. Amino acid sequences which result in a corresponding manner from SEQ ID No. 2 are also a constituent of the invention.

In the same way, DNA sequences which hybridize with SEQ ID No. 1 or parts of SEQ ID No. 1 are a constituent of the invention. Finally, DNA sequences which are prepared by the polymerase chain reaction (PCR) using primers which result from SEQ ID No. 1 are a constituent of the invention. Such oligonucleotides typically have a length of at least 15 nucleotides.

Instructions for identifying DNA sequences by means of hybridization can be found by the expert, inter alia, in the handbook "The DIG System Users Guide for Filter Hybridization" from Boehringer Mannheim GmbH (Mannheim, Germany, 1993) and in Liebl et al. (International Journal of Systematic Bacteriology (1991) 41: 255–260). The hybridization takes place under stringent conditions, that is to say only hybrids in which the probe and target sequence, i. e. the polynucleotides treated with the probe, are at least 70% identical are formed. It is known that the stringency of the hybridization, including the washing steps, is influenced or determined by varying the buffer composition, the temperature and the salt concentration. The hybridization reaction is preferably carried out under a relatively low stringency compared with the washing steps (Hybaid Hybridisation Guide, Hybaid Limited, Teddington, UK, 1996).

A 5×SSC buffer at a temperature of approx. 50–68° C., for example, can be employed for the hybridization reaction. Probes can also hybridize here with polynucleotides which are less than 70% identical to the sequence of the probe. Such hybrids are less stable and are removed by washing under stringent conditions. This can be achieved, for example, by lowering the salt concentration to 2×SSC and optionally subsequently 0.5×SSC (The DIG System User's Guide for Filter Hybridisation, Boehringer Mannheim, Mannheim, Germany, 1995) a temperature of approx. 50–68° C. being established. It is optionally possible to lower the salt concentration to 0.1×SSC. Polynucleotide fragments which are, for example, at least 70% or at least 80% or at least 90% to 95% identical to the sequence of the probe employed can be isolated by increasing the hybridization temperature stepwise from 50 to 68° C. in steps of approx. 1–2° C. Further instructions on hybridization are obtainable on the market in the form of so-called kits (e.g. DIG Easy Hyb from Roche Diagnostics GmbH, Mannheim, Germany, Catalogue No. 1603558).

Instructions for amplification of DNA sequences with the aid of the polymerase chain reaction (PCR) can be found by the expert, inter alia, in the handbook by Gait: Oligonucleotide Synthesis: A Practical Approach (IRL Press, Oxford, UK, 1984) and in Newton and Graham: PCR (Spektrum Akademischer Verlag, Heidelberg, Germany, 1994).

In the work on the present invention, it has been found that coryneform bacteria produce amino acids in an improved manner after over-expression of the sigE gene.

To achieve an over-expression, the number of copies of the corresponding genes can be increased, or the promoter and regulation region or the ribosome binding site upstream of the structural gene can be mutated. Expression cassettes which are incorporated upstream of the structural gene act in the same way. By inducible promoters, it is additionally possible to increase the expression in the course of fermentative amino acid production. The expression is likewise improved by measures to prolong the life of the m-RNA. Furthermore, the enzyme activity is also increased by preventing the degradation of the enzyme protein. The genes or gene constructs can either be present in plasmids with a varying number of copies, or can be integrated and amplified in the chromosome. Alternatively, an over-expression of the genes in question can furthermore be achieved by changing the composition of the media and the culture procedure.

Instructions in this context can be found by the expert, inter alia, in Martin et al. (Bio/Technology 5, 137–146 (1987)), in Guerrero et al. (Gene 138, 35–41 (1994)), in Tsuchiya and Morinaga (Bio/Technology 6, 428–430 (1988)), in Eikmanns et al. (Gene 102, 93–98 (1991)), in EP 0 472 869, in U.S. Pat. No. 4,601,893, in Schwarzer and P ühler (Bio/Technology 9, 84–87 (1991), in Reinscheid et al. (Applied and Environmental Microbiology 60, 126–132 (1994)), in LaBarre et al. (Journal of Bacteriology 175, 1001–1007 (1993)), in WO 96/15246, in Malumbres et al. (Gene 134, 15–24 (1993)), in JP-A-10-229891, in Jensen and Hammer (Biotechnology and Bioengineering 58, 191–195 (1998)), in Makrides (Microbiological Reviews 60:512–538 (1996)) and in known textbooks of genetics and molecular biology.

By way of example, for enhancement the sigE gene according to the invention was over-expressed with the aid of episomal plasmids. Suitable plasmids are those which are replicated in coryneform bacteria. Numerous known plasmid vectors, such as e.g. pZ1 (Menkel et al., Applied and Environmental Microbiology (1989) 64: 549–554), pEKEx1 (Eikmanns et al., Gene 102:93–98 (1991)) or pHS2-1 (Sonnen et al., Gene 107:69–74 (1991)) are based on the cryptic plasmids pHM1519, pBL1 or pGA1. Other plasmid vectors, such as e.g. those based on pCG4 (U.S. Pat. No. 4,489,160), or pNG2 (Serwold-Davis et al., FEMS Microbiology Letters 66, 119–124 (1990)), or pAG1 (U.S. Pat. No. 5,158,891), can be used in the same manner.

Plasmid vectors which are furthermore suitable are also those with the aid of which the process of gene amplification by integration into the chromosome can be used, as has been described, for example, by Reinscheid et al. (Applied and Environmental Microbiology 60, 126–132 (1994)) for duplication or amplification of the hom-thrB operon. In this method, the complete gene is cloned in a plasmid vector which can replicate in a host (typically E. coli), but not in C. glutamicum. Possible vectors are, for example, pSUP301 (Simon et al., Bio/Technology 1, 784–791 (1983)), pK18mob or pK19mob (Schäfer et al., Gene 145, 69–73 (1994)), pGEM-T (Promega corporation, Madison, Wis., USA), pCR2.1-TOPO (Shuman (1994). Journal of Biological Chemistry 269:32678–84; U.S. Pat. No. 5,487,993), pCR®Blunt (Invitrogen, Groningen, Holland; Bernard et al., Journal of Molecular Biology, 234: 534–541 (1993)), pEM1 (Schrumpf et al, 1991, Journal of Bacteriology 173:4510–4516) or pBGS8 (Spratt et al.,1986, Gene 41: 337–342). The plasmid vector which contains the gene to be amplified is then transferred into the desired strain of C. glutamicum by conjugation or transformation. The method of conjugation is described, for example, by Schäfer et al. (Applied and Environmental Microbiology 60, 756–759

(1994)). Methods for transformation are described, for example, by Thierbach et al. (Applied Microbiology and Biotechnology 29, 356–362 (1988)), Dunican and Shivnan (Bio/Technology 7, 1067–1070 (1989)) and Tauch et al. (FEMS Microbiological Letters 123, 343–347 (1994)). After homologous recombination by means of a "cross over" event, the resulting strain contains at least two copies of the gene in question.

In addition, it may be advantageous for the production of L-amino acids to enhance, in particular over-express one or more enzymes of the particular biosynthesis pathway, of glycolysis, of anaplerosis, of the citric acid cycle, of the pentose phosphate cycle, of amino acid export and optionally regulatory proteins, in addition to the sigE gene.

Thus, for example, for the preparation of L-amino acids, in addition to enhancement of the sigE gene, one or more genes chosen from the group consisting of the dapA gene which codes for dihydrodipicolinate synthase (EP-B 0 197 335), the gap gene which codes for glyceraldehyde 3-phosphate dehydrogenase (Eikmanns (1992), Journal of Bacteriology 174:6076–6086), the tpi gene which codes for triose phosphate isomerase (Eikmanns (1992), Journal of Bacteriology 174:6076–6086), the pgk gene which codes for 3-phosphoglycerate kinase (Eikmanns (1992), Journal of Bacteriology 174:6076–6086), the zwf gene which codes for glucose 6-phosphate dehydrogenase (JP-A-09224661), the pyc gene which codes for pyruvate carboxylase (DE-A-198 31 609), the mqo gene which codes for malate-quinone oxidoreductase (Molenaar et al., European Journal of Biochemistry 254, 395–403 (1998)), the lysC gene which codes for a feed-back resistant aspartate kinase (Accession No. P26512; EP-A-0699759), the lysE gene which codes for lysine export (DE-A-195 48 222), the hom gene which codes for homoserine dehydrogenase (EP-A 0131171), the ilvA gene which codes for threonine dehydratase (Möckel et al., Journal of Bacteriology (1992) 8065–8072)) or the ilvA(Fbr) allele which codes for a "feed back resistant" threonine dehydratase (Möckel et al., (1994) Molecular Microbiology 13: 833–842), the ilvBN gene which codes for acetohydroxy-acid synthase (EP-B 0356739), the ilvD gene which codes for dihydroxy-acid dehydratase (Sahm and Eggeling (1999) Applied and Environmental Microbiology 65: 1973–1979), the zwa1 gene which codes for the Zwa1 protein (DE: 19959328.0, DSM 13115)

can be enhanced, in particular over-expressed.

It may furthermore be advantageous for the production of L-amino acids, in addition to the enhancement of the sigE gene, for one or more of the genes chosen from the group consisting of:

the pck gene which codes for phosphoenol pyruvate carboxykinase (DE 199 50 409.1; DSM 13047), the pgi gene which codes for glucose 6-phosphate isomerase (U.S. Ser. No. 09/396,478; DSM 12969), the poxB gene which codes for pyruvate oxidase (DE: 1995 1975.7; DSM 13114), the zwa2 gene which codes for the Zwa2 protein (DE: 19959327.2, DSM 13113)

to be attenuated, in particular for the expression thereof to be reduced.

In addition to over-expression of the sigE gene it may furthermore be advantageous for the production of amino acids to eliminate undesirable side reactions (Nakayama: "Breeding of Amino Acid Producing Micro-organisms", in: Overproduction of Microbial Products, Krumphanzl, Sikyta, Vanek (eds.), Academic Press, London, UK, 1982).

The invention also provides the microorganisms prepared according to the invention, and these can be cultured continuously or discontinuously in the batch process (batch culture) or in the fed batch (feed process) or repeated fed batch process (repetitive feed process) for the purpose of production of amino acids. A summary of known culture methods is described in the textbook by Chmiel (Bioprozesstechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must meet the requirements of the particular strains in a suitable manner. Descriptions of culture media for various microorganisms are contained in the handbook "Manual of Methods for General Bacteriology" of the American Society for Bacteriology (Washington D.C., USA, 1981).

Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substances can be used individually or as a mixture.

Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture.

Phosphoric acid, potassium dihydrogen phosphate or dipotassium hydrogen phosphate or the corresponding sodium-containing salts can be used as the source of phosphorus. The culture medium must furthermore comprise salts of metals, such as e. g. magnesium sulfate or iron sulfate, which are necessary for growth. Finally, essential growth substances, such as amino acids and vitamins, can be employed in addition to the above-mentioned substances. Suitable precursors can moreover be added to the culture medium. The starting substances mentioned can be added to the culture in the form of a single batch, or can be fed in during the culture in a suitable manner.

Basic compounds, such as sodium hydroxide, potassium hydroxide, ammonia or aqueous ammonia, or acid compounds, such as phosphoric acid or sulfuric acid, can be employed in a suitable manner to control the pH of the culture. Antifoams, such as e.g. fatty acid polyglycol esters, can be employed to control the development of foam. Suitable substances having a selective action, such as e.g. antibiotics, can be added to the medium to maintain the stability of plasmids. To maintain aerobic conditions, oxygen or oxygen-containing gas mixtures, such as e.g. air, are introduced into the culture. The temperature of the culture is usually 20° C. to 45° C., and preferably 25° C. to 40° C. Culturing is continued until a maximum of the desired product has formed. This target is usually reached within 10 hours to 160 hours.

Methods for the determination of L-amino acids are known from the prior art. The analysis can thus be carried out, for example, as described by Spackman et al. (Analytical Chemistry, 30, (1958), 1190) by ion exchange chromatography with subsequent ninhydrin derivation, or it can be carried out by reversed phase HPLC, for example as described by Lindroth et al. (Analytical Chemistry (1979) 51: 1167–1174).

The process according to the invention is used for fermentative preparation of amino acids.

The following microorganism was deposited as a pure culture on 11th Apr. 2001 at the Deutsche Sammlung für Mikroorganismen und Zellkulturen (DSMZ=German Collection of Microorganisms and Cell Cultures, Braunschweig, Germany) in accordance with the Budapest Treaty:

Corynebacterium glutamicum DSM5715/pEC-T18mob2sigEexp as DSM 14229.

The present invention is explained in more detail in the following with the aid of embodiment examples.

The isolation of plasmid DNA from Escherichia coli and all techniques of restriction, Klenow and alkaline phosphatase treatment were carried out by the method of Sambrook et al. (Molecular Cloning. A Laboratory Manual (1989) Cold Spring Harbor Laboratory Press, Cold Spring Harbor, N.Y., USA). Methods for transformation of Escherichia coli are also described in this handbook.

The composition of the usual nutrient media, such as LB or TY medium, can also be found in the handbook by Sambrook et al.

EXAMPLE 1
Preparation of a Genomic Cosmid Gene Library from Corynebacterium glutamicum ATCC 13032

Chromosomal DNA from Corynebacterium glutamicum ATCC 13032 was isolated as described by Tauch et al. (1995, Plasmid 33:168–179) and partly cleaved with the restriction enzyme Sau3AI (Amersham Pharmacia, Freiburg, Germany, Product Description Sau3AI, Code no. 27-0913-02). The DNA fragments were dephosphorylated with shrimp alkaline phosphatase (Roche Diagnostics GmbH, Mannheim, Germany, Product Description SAP, Code no. 1758250). The DNA of the cosmid vector Super-Cos1 (Wahl et al. (1987) Proceedings of the National Academy of Sciences USA 84:2160–2164), obtained from Stratagene (La Jolla, USA, Product Description SuperCos1 Cosmid Vector Kit, Code no. 251301) was cleaved with the restriction enzyme XbaI (Amersham Pharmacia, Freiburg, Germany, Product Description XbaI, Code no. 27-0948-02) and likewise dephosphorylated with shrimp alkaline phosphatase.

The cosmid DNA was then cleaved with the restriction enzyme BamHI (Amersham Pharmacia, Freiburg, Germany, Product Description BamHI, Code no. 27-0868-04). The cosmid DNA treated in this manner was mixed with the treated ATCC13032 DNA and the batch was treated with T4 DNA ligase (Amersham Pharmacia, Freiburg, Germany, Product Description T4-DNA-Ligase, Code no. 27-0870-04). The ligation mixture was then packed in phages with the aid of Gigapack II XL Packing Extract (Stratagene, La Jolla, USA, Product Description Gigapack II XL Packing Extract, Code no. 200217).

For infection of the E coli strain NM554 (Raleigh et al. 1988, Nucleic Acid Research 16:1563–1575) the cells were taken up in 10 mM MgSO$_4$ and mixed with an aliquot of the phage suspension. The infection and titering of the cosmid library were carried out as described by Sambrook et al. (1989, Molecular Cloning: A laboratory Manual, Cold Spring Harbor), the cells being plated out on LB agar (Lennox, 1955, Virology, 1:190) with 100 mg/l ampicillin. After incubation overnight at 37° C., recombinant individual clones were selected.

EXAMPLE 2
Isolation and Sequencing of the sigE Gene

The cosmid DNA of an individual colony was isolated with the Qiaprep Spin Miniprep Kit (Product No. 27106, Qiagen, Hilden, Germany) in accordance with the manufacturer's instructions and partly cleaved with the restriction enzyme Sau3AI (Amersham Pharmacia, Freiburg, Germany, Product Description Sau3AI, Product No. 27-0913-02). The DNA fragments were dephosphorylated with shrimp alkaline phosphatase (Roche Diagnostics GmbH, Mannheim, Germany, Product Description SAP, Product No. 1758250). After separation by gel electrophoresis, the cosmid fragments in the size range of 1500 to 2000 bp were isolated with the QiaExII Gel Extraction Kit (Product No. 20021, Qiagen, Hilden, Germany).

The DNA of the sequencing vector pZero-1, obtained from Invitrogen (Groningen, Holland, Product Description Zero Background Cloning Kit, Product No. K2500-01), was cleaved with the restriction enzyme BamHI (Amersham Pharmacia, Freiburg, Germany, Product Description BamHI, Product No. 27-0868-04). The ligation of the cosmid fragments in the sequencing vector pZero-1 was carried out as described by Sambrook et al. (1989, Molecular Cloning: A Laboratory Manual, Cold Spring Harbor), the DNA mixture being incubated overnight with T4 ligase (Pharmacia Biotech, Freiburg, Germany). This ligation mixture was then electroporated (Tauch et al. 1994, FEMS Microbiol Letters, 123:343–7) into the E. coli strain DH5αMCR (Grant, 1990, Proceedings of the National Academy of Sciences U.S.A., 87:4645–4649) and plated out on LB agar (Lennox, 1955, Virology, 1:190) with 50 mg/l zeocin.

The plasmid preparation of the recombinant clones was carried out with the Biorobot 9600 (Product No. 900200, Qiagen, Hilden, Germany). The sequencing was carried out by the dideoxy chain termination method of Sanger et al. (1977, Proceedings of the National Academy of Sciences U.S.A., 74:5463–5467) with modifications according to Zimmermann et al. (1990, Nucleic Acids Research, 18:1067). The "RR dRhodamin Terminator Cycle Sequencing Kit" from PE Applied Biosystems (Product No. 403044, Weiterstadt, Germany) was used. The separation by gel electrophoresis and analysis of the sequencing reaction were carried out in a "Rotiphoresis NF Acrylamide/Bisacrylamide" Gel (29:1) (Product No. A124.1, Roth, Karlsruhe, Germany) with the "ABI Prism 377" sequencer from PE Applied Biosystems (Weiterstadt, Germany).

The raw sequence data obtained were then processed using the Staden program package (1986, Nucleic Acids Research, 14:217–231) version 97-0. The individual sequences of the pzero1 derivatives were assembled to a continuous contig.

The computer-assisted coding region analysis was prepared with the XNIP program (Staden, 1986, Nucleic Acids Research, 14:217–231).

The resulting nucleotide sequence is shown in SEQ ID No. 1. Analysis of the nucleotide sequence showed an open reading frame of 651 base pairs, which was called the sigE gene. The sigE gene codes for a protein of 216 amino acids (SEQ ID NO. 2).

The DNA sections lying upstream and downstream of SEQ ID NO. 1, which are shown in SEQ ID NO. 3 and SEQ ID NO. 4, were identified in the same manner. The sigE gene region extended by SEQ ID NO. 3 and SEQ ID NO. 4 is shown in SEQ ID NO. 5.

EXAMPLE 3

Preparation of a Shuttle Vector pEC-T18mob2sigEexp for Enhancement of the sigE Gene in C. glutamicum 3.1. Cloning of the sigE Gene From the strain ATCC 13032, chromosomal DNA was isolated by the method of Eikmanns et al. (Microbiology 140: 1817–1828 (1994)). On the basis of the sequence of the sigE gene known for C. glutamicum from example 2, the following oligonucleotides were chosen for the polymerase chain reaction (see SEQ ID No. 7 and SEQ ID No. 8).

```
sigE1:
5' TAG TCA CCA CGG TTA AGC CT 3' sigE2:
5' GCC TTG GTT CTT ACG AAC TG 3'
```

The primers shown were synthesized by ARK Scientific GmbH Biosystems (Darmstadt, Germany) and the PCR reaction was carried out by the standard PCR method of Innis et al. (PCR protocols. A guide to methods and applications, 1990, Academic Press) with Taq-Polymerase from Qiagen (Hilden, Germany). With the aid of the polymerase chain reaction, the primers allow amplification of a DNA fragment approx. 2.03 kb in size, which carries the sigE gene.

The amplified DNA fragment of approx. 2.03 kb in size which carries the sigE gene was ligated with the TOPO TA Cloning® Kit from Invitrogen Corporation (Carlsbad, Calif., USA) in the vector pCR®2.1TOPO (Bernard et al., Journal of Molecular Biology, 234: 534–541 (1993)). The *E. coli* strain Top10 (Grant et al., Proceedings of the National Academy of Sciences USA, 87 (1990) 4645–4649) was then transformed with the ligation batch in accordance with the instructions of the manufacturer of the kit (Invitrogen Corporation, Carlsbad, Calif., USA). Selection of plasmid-carrying cells was carried out by plating out the transformation batch on LB Agar (Sambrook et al., Molecular cloning: a laboratory manual. $2^{nd}$ Ed. Cold Spring Harbor Laboratory Press, Cold Spring Harbor, N.Y., 1989), which had been supplemented with 50 mg/l kanamycin. Plasmid DNA was isolated from a transformant with the aid of the QIAprep Spin Miniprep Kit from Qiagen (Hilden, Germany) and checked by treatment with the restriction enzyme SphI and EcoRI with subsequent agarose gel electrophoresis (0.8%). The DNA sequence of the amplified DNA fragment was checked by sequencing. The plasmid was called pCR2.1sigEexp. The strain was called *E. coli* Top10/pCR2.1sigEexp.

3.2. Preparation of the *E. coli-C. glutamicum* Shuttle Vector pEC-T18mob2

The *E. coli-C. glutamicum* shuttle vector was constructed according to the prior art. The vector contains the replication region reg of the plasmid pGA1 including the replication effector per (U.S. Pat. No. 5,175,108; Nesvera et al., Journal of Bacteriology 179, 1525–1532 (1997)), the tetracycline resistance-imparting tetA(Z) gene of the plasmid pAG1 (U.S. Pat. No. 5,158,891; gene library entry at the National Center for Biotechnology Information (NCBI, Bethesda, Md., USA) with the accession number AF121000), the replication region oriV of the plasmid pMB1 (Sutcliffe, Cold Spring Harbor Symposium on Quantitative Biology 43, 77–90 (1979)), the lacZα gene fragment including the lac promoter and a multiple cloning site (mcs) (Norrander, J. M. et al. Gene 26, 101–106 (1983)) and the mob region of the plasmid RP4 (Simon et al.,(1983) Bio/Technology 1:784–791). The vector constructed was transformed in the *E. coli* strain DH5α (Hanahan, In: DNA cloning. A Practical Approach. Vol. I. IRL-Press, Oxford, Washington D.C., USA).

Selection for plasmid-carrying cells was made by plating out the transformation batch on LB agar (Sambrook et al., Molecular cloning: A Laboratory Manual. $2^{nd}$ Ed. Cold Spring Harbor Laboratory Press, Cold Spring Harbor, N.Y.), which had been supplemented with 5 mg/l tetracycline. Plasmid DNA was isolated from a transformant with the aid of the QIAprep Spin Miniprep Kit from Qiagen and checked by restriction with the restriction enzymes EcoRI and HindIII and subsequent agarose gel electrophoresis (0.8%). The plasmid was called pEC-T18mob2 and is shown in FIG. 1.

3.3. Cloning of sigE in the *E. coli-C. glutamicum* Shuttle Vector pEC-T18mob2

The *E. coli -C. glutamicum* shuttle vector pEC-T18mob2 described in example 3.2 was used as the vector. DNA of this plasmid was cleaved completely with the restriction enzymes BamHI and SalI and then dephosphorylated with shrimp alkaline phosphatase (Roche Diagnostics GmbH, Mannheim, Germany, Product Description SAP, Product No. 1758250).

The sigE gene was isolated from the plasmid pCR2.1sigEexp described in example 3.1. by complete cleavage with the enzymes BamHI and SalI. The sigE fragment 1930 bp in size was isolated from the agarose gel with the QiaExII Gel Extraction Kit (Product No. 20021, Qiagen, Hilden, Germany).

The sigE fragment obtained in this manner was mixed with the prepared vector pEC-T18mob2 and the batch was treated with T4 DNA ligase (Amersham Pharmacia, Freiburg, Germany, Product Description T4-DNA-Ligase, Code no. 27-0870-04). The ligation batch was transformed in the *E. coli* strain DH5αMCR (Hanahan, In: DNA cloning. A Practical Approach. Vol. I. IRL-Press, Oxford, Washington D.C., USA). Selection of plasmid-carrying cells was made by plating out the transformation batch on LB agar (Lennox, 1955, Virology, 1:190) with 5 mg/l tetracycline. After incubation overnight at 37° C., recombinant individual clones were selected. Plasmid DNA was isolated from a transformant with the Qiaprep Spin Miniprep Kit (Product No. 27106, Qiagen, Hilden, Germany) in accordance with the manufacturer's instructions and cleaved with the restriction enzymes BamHI and SalI to check the plasmid by subsequent agarose gel electrophoresis. The plasmid obtained was called pEC-T18mob2sigEexp. It is shown in FIG. 2.

EXAMPLE 4

Transformation of the Strain DSM5715 with the Plasmid pEC-T18mob2sigEexp

The strain DSM5715 was transformed with the plasmid pEC-T18mob2sigEexp using the electroporation method described by Liebl et al., (FEMS Microbiology Letters, 53:299–303 (1989)). Selection of the transformants took place on LBHIS agar comprising 18.5 g/l brain-heart infusion broth, 0.5 M sorbitol, 5 g/l Bacto-tryptone, 2.5 g/l Bacto-yeast extract, 5 g/l NaCl and 18 g/l Bacto-agar, which had been supplemented with 5 mg/l tetracycline. Incubation was carried out for 2 days at 33° C. Plasmid DNA was isolated from a transformant by conventional methods (Peters-Wendisch et al., 1998, Microbiology, 144, 915–927), cleaved with the restriction endonucleases BamHI and SalI, and the plasmid was checked by subsequent agarose gel electrophoresis. The strain obtained was called DSM5715/pEC-T18mob2sigEexp.

EXAMPLE 5
Preparation of Lysine

The *C. glutamicum* strain DSM5715/pEC-T18mob2sigEexp obtained in example 4 was cultured in a nutrient medium suitable for the production of lysine and the lysine content in the culture supernatant was determined.

For this, the strain was first incubated on an agar plate with the corresponding antibiotic (brain-heart agar with tetracycline (5 mg/l)) for 24 hours at 33° C. Starting from this agar plate culture, a pre-culture was seeded (10 ml medium in a 100 ml conical flask). The complete medium CgIII was used as the medium for the pre-culture.

| Medium Cg III | |
|---|---|
| NaCl | 2.5 g/l |
| Bacto-Peptone | 10 g/l |
| Bacto-Yeast extract | 10 g/l |
| Glucose (autoclaved separately) | 2% (w/v) |
| The pH was brought to pH 7.4 | |

Tetracycline (5 mg/l) was added to this. The pre-culture was incubated for 16 hours at 33° C. at 240 rpm on a shaking machine. A main culture was seeded from this pre-culture such that the initial OD (660 nm) of the main culture was 0.05. Medium MM was used for the main culture.

| Medium MM | |
|---|---|
| CSL (corn steep liquor) | 5 g/l |
| MOPS (morpholinopropanesulfonic acid) | 20 g/l |

| -continued | |
|---|---|
| Medium MM | |
| Glucose (autoclaved separately) | 50 g/l |
| $(NH_4)_2SO_4$ | 25 g/l |
| $KH_2PO_4$ | 0.1 g/l |
| $MgSO_4 * 7 H_2O$ | 1.0 g/l |
| $CaCl_2 * 2 H_2O$ | 10 mg/l |
| $FeSO_4 * 7 H_2O$ | 10 mg/l |
| $MnSO_4 * H_2O$ | 5.0 mg/l |
| Biotin (sterile-filtered) | 0.3 mg/l |
| Thiamine * HCl (sterile-filtered) | 0.2 mg/l |
| L-Leucine (sterile-filtered) | 0.1 g/l |
| $CaCO_3$ | 25 g/l |

The CSL, MOPS and the salt solution were brought to pH 7 with aqueous ammonia and autoclaved. The sterile substrate and vitamin solutions were then added, as well as the $CaCO_3$ autoclaved in the dry state.

Culturing is carried out in a 10 ml volume in a 100 ml conical flask with baffles. Tetracycline (5 mg/l) was added. Culturing was carried out at 33° C. and 80% atmospheric humidity.

After 48 hours, the OD was determined at a measurement wavelength of 660 nm with a Biomek 1000 (Beckmann Instruments GmbH, Munich). The amount of lysine formed was determined with an amino acid analyzer from Eppendorf-BioTronik (Hamburg, Germany) by ion exchange chromatography and post-column derivation with ninhydrin detection.

The result of the experiment is shown in Table 1.

TABLE 1

| Strain | OD (660 nm) | Lysine HCl g/l |
|---|---|---|
| DSM5715/pEC-T18mob2 | 12.2 | 13.14 |
| DSM5715/pEC-T18mob2sigEexp | 13.07 | 14.09 |

What is claimed is:

1. A method for the preparation of L-amino acids, comprising:
   culturing coryneform bacteria, which include an overexpressed sigE gene having a polynucleotide sequence which encodes the amino acid sequence of SEQ ID NO: 2, in a medium suitable for the expression of sigE to thereby produce L-amino acids wherein overexpression of the sigE gene is accomplished by increasing the copy number of said gene or operatively linking said gene to a promoter.

2. The method according to claim 1, further comprising isolating the L-amino acids.

3. The method according to claim 1, wherein the coryneform bacteria produce L-lysine.

4. The method according to claim 1, wherein the bacteria have been transformed with a plasmid vector which comprises the nucleotide sequence of SEQ ID NO: 1.

5. The method according to claim 1, wherein the bacteria are *Corynebacterium glutamicum*.

6. The process according to claim 1, further comprising overexpressing at least one *C. glutamicum* gene selected from the group consisting of:
   a) the dapA gene which codes for dihydrodipicolinate synthase,
   b) the gap gene which codes for glyceraldehyde 3-phosphate dehydrogenase,
   c) the tpi gene which codes for triose phosphate isomerase,
   d) the pgk gene which codes for 3-phosphoglycerate kinase,
   e) the zwf gene which codes for glucose 6-phosphate dehydrogenase,
   f) the pyc gene which codes for pyruvate carboxylase,
   g) the mqo gene which codes for malate-quinone oxidoreductase,
   h) the lysC gene which codes for feed-back resistant aspartate kinase,
   i) the lysE gene which codes for a protein that exports lysine,
   j) the hom gene which codes for homoserine dehydrogenase,
   k) the ilvA gene which codes for threonine dehydratase or the ilvA(Fbr) allele which codes for feed-back resistant threonine dehydratase,
   l) the ilvBN gene which code for acetohydroxy-acid synthase, and
   m) the ilvD gene which codes for dihydroxy-acid dehydratase.

7. The process according to claim 1 wherein the coryneform bacterium is *C. glutamicum*, the process further comprising deleting at least one *C. glutamicum* gene selected from the group consisting of:
   a) the pck gene which codes for phosphoenol pyruvate carboxykinase,
   b) the pgi gene which codes for glucose 6-phosphate isomerase, and
   c) the poxB gene which codes for pyruvate oxidase.

8. A process for the production of an L-amino acid comprising:
   a) culturing a coryneform bacterium under conditions suitable for overexpression of a nucleic acid comprising nucleotides 302 to 949 of SEQ ID NO: 1; and
   (b) isolating the L-amino acid
   wherein overexpression occurs by increasing the copy number of said nucleic acid or operatively linking said nucleic acid to a promoter.

9. A process for the production of an L-amino acid comprising:
  (a) culturing a coryneform bacterium under conditions suitable for overexpression of the sigE gene having the nucleic acid sequence as set forth in SEQ ID NO: 1; and
  (b) isolating the L-amino acid
  wherein overexpression occurs by increasing the copy number of said gene or operatively linking said gene to a promoter.

10. The process according to claim 9, wherein said L-amino acid is L-Iysine.

11. The process according to claim 9, wherein said coryneform bacteria have been transformed with a plasmid vector which comprises the nucleotide sequence of SEQ ID NO: 1.

12. The process according to claim 9, further comprising overexpressing at least one *C. glutamicum* gene selected from the group consisting of:
  a) the dapA gene which codes for dihydrodipicolinate synthase,
  b) the gap gene which codes for glyceraldehyde 3-phosphate dehydrogenase,
  c) the tpi gene which codes for triose phosphate isomerase,
  d) the pgk gene which codes for 3-phosphoglycerate kinase,
  e) the zwf gene which codes for glucose 6-phosphate dehydrogenase,
  f) the pyc gene which codes for pyruvate carboxylase,
  g) the mqo gene which codes for malate-quinone oxidoreductase,
  h) the lysC gene which codes for feed-back resistant aspartate kinase,
  i) the lysE gene which codes for a protein that exports lysine,
  j) the horn gene which codes for homoserine dehydrogenase,
  k) the ilvA gene which codes for threonine dehydratase or the ilvA(Fbr) allele which codes for feed-back resistant threonine dehydratase,
  l) the ilvBN gene which code for acetohydroxy-acid synthase, and
  m) the ilvD gene which codes for dihydroxy-acid dehydratase.

13. The process according to claim 9, wherein said coryneform bacteria are of the species *Corynebacterium glutamicum*.

14. The process according to claim 9 wherein the coryneform bacterium is *C. glutamicum*, the process further comprising deleting at least one *C. glutamicum* gene selected from the group consisting of:
  a) the pck gene which codes for phosphoenol pyruvate carboxykinase,
  b) the pgi gene which codes for glucose 6-phosphate isomerase, and
  c) the poxB gene which codes for pyruvate oxidase.

* * * * *